US010568325B2

(12) United States Patent
Salminen et al.

(10) Patent No.: US 10,568,325 B2
(45) Date of Patent: *Feb. 25, 2020

(54) NATURALLY-DERIVED SURFACE SANITIZER AND DISINFECTANT

(71) Applicant: PRONATURAL BRANDS, LLC, Victor, NY (US)

(72) Inventors: William Salminen, Sarasota, FL (US); Gary Russotti, Boca Raton, FL (US); Richard Aab, Fairport, NY (US); Robert Tuchrelo, Williamson, NY (US); Jeffrey Cahoon, Williamson, NY (US)

(73) Assignee: ProNatural Brands, LLC, Victor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/059,307

(22) Filed: Aug. 9, 2018

(65) Prior Publication Data
US 2018/0343861 A1    Dec. 6, 2018

Related U.S. Application Data

(62) Division of application No. 14/510,778, filed on Oct. 9, 2014, now Pat. No. 10,076,115.

(51) Int. Cl.
*A01N 41/04* (2006.01)
*A01N 25/22* (2006.01)
*A01N 37/02* (2006.01)
*A01N 37/36* (2006.01)

(52) U.S. Cl.
CPC ............ *A01N 41/04* (2013.01); *A01N 25/22* (2013.01); *A01N 37/02* (2013.01); *A01N 37/36* (2013.01)

(58) Field of Classification Search
None
See application file for complete search history.

(56) References Cited

U.S. PATENT DOCUMENTS

| | | |
|---|---|---|
| 4,404,040 A | 9/1983 | Wang |
| 4,715,980 A | 12/1987 | Lopes et al. |
| 4,975,217 A | 12/1990 | Brown-Skrobot et al. |
| 5,143,720 A | 9/1992 | Lopes |
| 5,280,042 A | 1/1994 | Lopes |
| 5,330,769 A | 7/1994 | McKinzie et al. |
| 5,403,587 A | 4/1995 | McCue et al. |
| 5,436,008 A | 7/1995 | Richter et al. |
| 5,460,833 A | 10/1995 | Andrews et al. |
| 5,490,992 A | 2/1996 | Andrews et al. |
| 5,705,461 A | 1/1998 | Murch et al. |
| 5,942,478 A | 8/1999 | Lopes |
| 6,019,905 A | 2/2000 | Waggoner |
| 6,071,961 A | 6/2000 | Wider |
| 6,190,675 B1 * | 2/2001 | Beerse .................. A61K 8/347 424/401 |
| 6,262,038 B1 | 7/2001 | Pierce et al. |
| 6,345,634 B1 | 2/2002 | Murch et al. |
| 6,472,358 B1 | 10/2002 | Richter et al. |
| 6,553,779 B1 | 4/2003 | Boyer et al. |
| 6,753,305 B2 | 6/2004 | Raso et al. |
| 6,846,498 B2 | 1/2005 | DeAth et al. |
| 6,867,233 B2 | 3/2005 | Roselle et al. |
| 6,953,772 B2 | 10/2005 | Lopes |
| 7,090,882 B2 | 8/2006 | Koefod et al. |
| 7,642,227 B2 | 1/2010 | Kurtz |
| 7,851,430 B2 | 12/2010 | Kurtz |
| 8,147,877 B2 | 4/2012 | DeAth et al. |
| 8,205,460 B2 | 6/2012 | Russo et al. |
| 2002/0132742 A1 | 9/2002 | Mizuki |
| 2002/0187918 A1 | 12/2002 | Urban |

(Continued)

FOREIGN PATENT DOCUMENTS

| | | |
|---|---|---|
| EP | 1252283 B1 | 7/2007 |
| WO | WO-1996009761 A1 | 4/1996 |
| WO | WO-2014/152189 A1 | 9/2014 |

OTHER PUBLICATIONS

Zhao et al., Inactivation of *Salmonella* and *Escherichia coli* O157:H7 on Lettuce and Poultry Skin by Combinations of Levulinic Acid and Sodium Dodecyl Sulfate, *Journal of Food Protection*, 72(5): 928-936 2009.
Health Pro Brands: "Fil Antibacterial Fruit & Vegetable Wash"—Oct. 3, 2006 (4 pages).
International Search Report and Written Opinion of the International Searching Authority in corresponding International Application No. PCT/US2015/051410, dated Dec. 28, 2015 (9 pages).
Supplementary European Search Report for European Application No. 15848915.3, dated Mar. 22, 2018.

*Primary Examiner* — Robert A Wax
*Assistant Examiner* — Randeep Singh
(74) *Attorney, Agent, or Firm* — Dinsmore & Shohl, LLP

(57) ABSTRACT

Food processing equipment, food contact surfaces, and non-food contact surfaces are sanitized or disinfected using an acid-anionic surfactant solution that has efficacy in hard water, is non-corrosive, and is stable at elevated temperatures. The sanitizing/disinfecting solution is prepared as a highly concentrated liquid and diluted to end use concentrations prior to application to food processing equipment or food or non-food contact surfaces. Efficacy in hard water is important for sanitizers and disinfectants that are diluted by the end user using potentially hard water. Stability at elevated temperatures is important for long-term storage and transportation. The diluted sanitizing/disinfecting solution exhibits strong antimicrobial activity against gram positive and gram negative bacteria even when diluted in hard water. The sanitizing/disinfecting solution exhibits low toxicity to humans and the environment since it is prepared from low toxicity ingredients that are readily biodegradable.

20 Claims, No Drawings

(56) References Cited

U.S. PATENT DOCUMENTS

| | | |
|---|---|---|
| 2009/0004122 A1 | 1/2009 | Modak et al. |
| 2010/0056416 A1* | 3/2010 | Scheuing .................. C11D 1/83 510/284 |
| 2010/0136148 A1 | 6/2010 | Saint Victor |
| 2011/0230385 A1* | 9/2011 | Murphy .................. C11D 1/94 510/382 |
| 2013/0253059 A1 | 9/2013 | Man et al. |
| 2014/0030203 A1 | 1/2014 | Dombeck |

* cited by examiner

NATURALLY-DERIVED SURFACE SANITIZER AND DISINFECTANT

PRIORITY CLAIM

This patent application is a divisional application of U.S. patent application Ser. No. 14/510,778, filed Oct. 9, 2014, which is incorporated by reference in its entirety.

FIELD OF THE INVENTION

This invention relates to the sanitization and disinfection of food processing equipment and food and non-food contact surfaces using a sanitizing/disinfecting solution that is formulated with naturally derived ingredients and maintains efficacy when diluted in hard water. The sanitizing/disinfecting solution is prepared as a highly concentrated liquid that is stable at elevated temperature, which is important for long-term storage and transportation. The sanitizer/disinfectant is non corrosive, which is important when sanitizing or disinfecting food processing equipment and food and non-food contact surfaces. The sanitizing/disinfecting solution exhibits low human and environmental toxicity since it is prepared from low toxicity ingredients that are readily biodegradable.

BACKGROUND OF THE INVENTION

Food processing equipment and food contact surfaces (e.g., tables and countertops) require sanitization or disinfection between food preparations, particularly when processing raw food such as cutting meat, in order to prevent cross-contamination and the spread of food-borne diseases. In addition, non-food contact surfaces benefit from sanitization and disinfection to limit pathogen loads and the spread of potentially infectious agents (e.g., in hospital, industrial, commercial, or household settings). Food processing equipment is often cleaned using one solution and then sanitized/disinfected with a separate solution. The solutions described in this invention allow the same solution to be used for cleaning and sanitizing/disinfecting since the solution has good cleaning power and strong antimicrobial efficacy. Sanitization greatly reduces the bioburden (e.g., bacteria, yeasts, molds, viruses) on the food or non-food contact surface and thereby reduces the likelihood of the spread of microbial diseases. Disinfection provides an even greater reduction in the amount of bioburden and in turn an even greater reduction in the likelihood of the spread of microbial diseases. The sanitizing/disinfecting solution described in this invention has the ability to function as a sanitizer and a disinfectant.

Many sanitizing and disinfecting compositions have been developed. Many are not approved for food contact surface use since they are formulated with ingredients that would be harmful if their residues on the food contact surface were transferred to food and were subsequently ingested by humans. Sanitizing and disinfecting compositions that are acceptable for food contact surface use are often corrosive to the food processing equipment or food contact surface since they often contain chlorine, chlorine dioxide, chlorinated or halogenated compounds, peracetic acid, or other corrosive ingredients. Therefore, there is a need for a low toxicity, non-corrosive sanitizing/disinfecting solution for food and non-food contact surface use.

Various patents have disclosed the antimicrobial properties of low pH (acidic)-anionic surfactant formulations, with some of the patents disclosing the use of low pH-anionic surfactant formulations on food contact surfaces. U.S. Pat. No. 6,953,772 discloses a food contact surface sanitizing solution including at least lactic acid and phosphoric acid, an anionic surfactant, and a sequestering agent. U.S. Pat. No. 5,143,720 discloses anhydrous sanitizing/disinfecting compositions including an acid and an anionic surfactant, and includes example anhydrous (dry) formulations including an acid, an anionic surfactant, and low concentrations of short chain fatty acids, although the purpose of including the fatty acids in the anhydrous formulations is not described. U.S. Pat. No. 4,715,980 discloses a food contact surface sanitizing composition including a dicarboxylic acid, another acid, and an anionic surfactant. U.S. Pat. No. 5,280,042 discloses food contact surface sanitizing and disinfecting compositions against cyst or oocyte forms of protozoa including an anionic surfactant and an acidic component. U.S. Pat. No. 6,867,233 discloses an acidic antimicrobial composition for use on food contact surfaces including an organic acid, an anionic surfactant, polypropylene glycol, and a carbonate. U.S. Pat. No. 7,851,430 discloses a food contact surface disinfecting composition containing an organic acid, an anionic surfactant, and a buffering agent.

U.S. Pat. No. 6,262,038 discloses a germicidal composition including a mixture of alpha-hydroxy fruit acid, anionic surfactant, and sophorose lipid biosurfactant for use on skin or hair. U.S. Pat. No. 5,490,992 discloses a disinfectant composition including a fatty acid monoester, an acid, and an anionic surfactant for use on poultry carcasses.

U.S. Pat. No. 4,404,040, discloses formulations for sanitizing dairy and brewery equipment using a solution comprising an aliphatic short chain fatty acid, a solubilizer (e.g., an anionic surfactant), and an acid. This patent further discloses the optional use of alcohols at low concentrations (≤0.2%) to help reduce the viscosity of the final concentrated solution.

A major limitation of the referenced low pH-anionic surfactant concentrate formulations is that their efficacy (cleaning ability and antimicrobial activity) may be adversely affected when diluted with hard water (e.g., water containing at least 300 ppm hardness ions such as calcium and magnesium, and especially at least 500 ppm hardness ions). Anionic surfactants such as sodium lauryl sulfate often have better hard water tolerance than soaps (saponified fatty acids); however, anionic surfactants may still suffer from reduced efficacy in hard water due to the formation of insoluble compounds when complexed with the calcium and magnesium ions typically present in hard water. In addition, acid-anionic surfactant formulations are inherently unstable due to hydrolysis of the anionic surfactant. This is particularly problematic at higher temperatures that may be encountered during storage of the product. It is accordingly an object of this invention to provide a stable, naturally-derived sanitizing/disinfecting solution that retains efficacy in hard water. In addition, the solution should exhibit low human and environmental toxicity and be non-corrosive.

SUMMARY OF THE INVENTION

In accordance with one embodiment, the invention is directed towards a sanitizing and disinfecting solution concentrate composition comprising: a) at least about 10 wt % water; b) one or more natural first organic acids at a total concentration of at least about 10 wt % and sufficient to provide a solution pH of from about 1.2-5.0; c) one or more sulfated fatty acid surfactants at a total concentration of at least about 5 wt %; d) one or more monocarboxylic fatty acids at a total concentration of at least about 0.1 wt %, wherein the one or more monocarboxylic fatty acids are distinct from the one or more natural first organic acids; and e) one or more alcohols at a total concentration of at least about 1 wt %. The invention further provides a method of cleaning, sanitizing, or disinfecting a food or non-food contact surface comprising diluting such a concentrate composition with at least 9 additional parts of water to one part of the concentrate composition to form a diluted solution having a pH of from about 1.2-5.0, and contacting the surface with the diluted solution.

The present invention involves sanitizing and disinfecting food and non-food contact surfaces using low pH, anionic surfactant formulations, which retain efficacy (cleaning ability and antimicrobial activity) when diluted to end-use concentrations in hard water. Furthermore, the formulations are prepared from naturally-derived ingredients and the formulations exhibit low human and environmental toxicity. The low environmental toxicity is particularly important for sanitizers/disinfectants that will be disposed of in commercial or residential waste water systems (e.g., rinsing of treated surfaces).

As described in the background information, this invention is partly predicated on the ability of low pH anionic surfactant formulations to kill microorganisms, such as food-borne bacterial pathogens. In accordance with the present invention, it has been discovered that adding a monocarboxylic fatty acid greatly improves the hard water tolerance of the sanitizing/disinfecting solution. Additionally, it has been discovered that further use of critical concentrations of organic alcohols provide elevated temperature stability to the formulations since both the anionic surfactant and fatty acid can separate out of solution during storage at elevated temperatures. The ingredients used to formulate the sanitizing/disinfecting solution are advantageously naturally-derived (i.e., found in nature, found in our bodies naturally, and/or undergone minimal chemical modifications [e.g., saponification or sulfation of fatty acids]) and exhibit low human and environmental toxicity when formulated and used at end-use concentrations. The formulations of the invention are further advantageously non-corrosive to stainless steel and aluminum, two materials often used in food and non-food contact surfaces, and leave little to no undesirable residue on the cleaned/sanitized/disinfected surface.

DETAILED DESCRIPTION OF THE INVENTION

The present invention pertains to the use of sanitizing and disinfecting formulations on food and non food contact surfaces and which are stable and have high tolerance to hard water (e.g., water having at least 300 ppm hardness ions such as calcium and magnesium, and especially water having at least 500 ppm hardness ions). The invention applies to all types of food and non-food contact surfaces such as food processing equipment, tables, countertops, cutting boards, inanimate medical surfaces (e.g., examination tables, lights, equipment), and other general surfaces found in healthcare, industrial, commercial, and household settings. Of critical importance is the tolerance to hard water since that allows end-users of the product to dilute the concentrated sanitizing/disinfecting solution in regular tap water and maintain excellent efficacy (cleaning and antimicrobial properties). In addition, the use of critical concentrations of organic alcohol provides stability during storage at elevated temperatures, which is important for both short- and long-term storage of solutions.

The sanitizers and disinfectants are comprised of an organic acid, a naturally-derived anionic surfactant, a natural fatty acid, and an organic alcohol. The organic acid and anionic surfactant provide strong antimicrobial properties necessary for food and non-food contact surface sanitizers and disinfectants. The fatty acid provides greatly improved efficacy in hard water and also reduces the foaming properties inherent with an anionic surfactant. A critical concentration of at least about 1 wt % of the organic alcohol provides elevated temperature stability to the formulations. Sodium sulfate or sodium bisulfate can be optionally included to further increase the efficacy in hard water. An essential oil can be optionally included to add a natural scent to the sanitizer/disinfectant.

All ingredients in the formulations are naturally derived (i.e., found in nature, found naturally in the human body, and/or undergone limited chemical modification [e.g., saponification or sulfation of a fatty acid]) and exhibit low human and environmental toxicity at end-use concentrations. The organic acid can be provided by one or more (e.g., combinations) of the following natural organic acids: citric acid, fumaric acid, humic acid, acetic acid, or ascorbic acid. Other similar natural organic acids can also be used. The concentrated liquid sanitizer/disinfectant formulation contains at least about 10 wt % of one or more natural first organic acids sufficient to provide a solution pH of from about 1.2-5.0, e.g., from about 10-40 wt % of such one or more natural first organic acid, preferably 15-35 wt %, and most preferably 21-30 wt %. Upon dilution to end-use concentrations, the diluted solution may contain, e.g., 0.01-4.0 wt % of the organic acid, preferably, 0.015-3.5 wt %, and most preferably, 0.021-3.0 wt %.

A naturally-derived, sulfated fatty acid (e.g., sodium lauryl sulfate) is used as the anionic surfactant. The concentrated liquid sanitizer/disinfectant formulation contains at least about 5 wt %, e.g., 5-30 wt %, of the anionic surfactant, preferably 8-20 wt %, and most preferably 10.5-12 wt %. Upon dilution to end-use concentrations, the diluted solution contains 0.005-3.0 wt % anionic surfactant, preferably, 0.008-2.0 wt %, and most preferably, 0.0105-1.2 wt %. The sulfated fatty acid in a particular embodiment comprises a C6-C18 alkyl sulfate, and in a more specific embodiment a C8-C14 alkyl sulfate. One or more (e.g., combinations) of any natural sulfated fatty acid (e.g., sodium lauryl sulfate, sodium caprylyl sulfate) can be used.

The monocarboxylic fatty acid can be provided by one or more (e.g., combinations) of the natural organic fatty acids, and in particular one or more saturated or unsaturated C6-C18 monocarboxylic acids. In a particular embodiment, the fatty acids can be provided by one or more of the following natural organic fatty acids: caproic acid, caprylic acid, capric acid, lauric acid, myristic acid, palmitic acid, stearic acid, oleic acid, linoleic acid, gamma-linolenic acid, hexadecatrienoic acid, alpha-linolenic acid, pinolenic acid, or stearidonic acid. Other similar natural fatty acids can also be used. The monocarboxylic fatty acid employed is distinct from the one or more natural first organic acids sufficient to provide a solution pH of from about 1.2-5.0, as such fatty acids are typically not capable of themselves providing such low pH. The concentrated liquid sanitizer/disinfectant formulation contains at least about 0.1 wt %, e.g., 0.1-5 wt % moncarboxylic fatty acid, preferably 0.5-3 wt %, and most preferably 1-3 wt %. Upon dilution to end-use concentrations, the diluted solution may contain, e.g., 0.0001-0.5 wt % monocarboxylic fatty acid, preferably, 0.0005-0.3 wt %, and most preferably, 0.001-0.2 wt %.

The organic alcohol can be provided by any organic alcohol, with ethanol and isopropanol being common examples. The concentrated liquid sanitizer/disinfectant formulation contains at least about 1 wt %, e.g., about 1-20 wt % alcohol, preferably 2-10 wt %, and most preferably 3-10 wt %. Upon dilution to end-use concentrations, the diluted solution may contain, e.g., 0.001-2 wt % alcohol, preferably, 0.0015-1.5 wt %, and most preferably, 0.002-0.7 wt %.

The concentrated solution is formulated to have a pH of from about 1.2 to 5, as a pH of greater than 5 results in a formulation that has poor antimicrobial properties, while a pH of less than about 1.2 results in strong irritating properties. Optionally, the pH of the resulting solution can be adjusted with a buffering agent, such that the pH of the final, diluted sanitizer/disinfectant solution remains under 5.0 (preferably from 1.8 to 4.0, most preferably 2.0-3.0) upon dilution since antibacterial efficacy is decreased as pH increases. The buffering agent can be selected from one of the following basic neutralizing agents: calcium carbonate, magnesium carbonate, potassium carbonate, potassium bicarbonate, sodium carbonate, or sodium bicarbonate. Alternatively, a combination of the organic acid, any sodium, potassium, magnesium, or calcium salt form of the organic acid, and/or one of the previously listed basic neutralizing agents can be combined in a ratio that results in the target pH.

Sodium sulfate or sodium bisulfate can optionally be added to the formulation to further increase tolerance to hard water. When combined with the fatty acid, sodium sulfate or sodium bisulfate increase the tolerance to hard water even more than the fatty acid or sulfate salts alone. When added, the sodium sulfate or sodium bisulfate is preferably present in the concentrated solution formulation at from about 0.1 to 10 wt %, more preferably about 2-8 wt %. While use of too much sodium sulfate or sodium bisulfate alone to provide hard water tolerance control can lead to solution gelling, the combination of a fatty acid with such relatively low levels of sodium sulfate or sodium bisulfate in the concentrate formulation further advantageously enables effective hard water tolerance control in a concentrate solution with acceptable viscosity. Upon dilution to end-use concentrations, the diluted solution may preferably contain, e.g., 0.001-1 wt % sodium sulfate or sodium bisulfate, preferably, 0.01-0.5 wt %, and most preferably, 0.02-0.1 wt %.

In further specific embodiments, the weight ratio of the one or more natural first organic acids sufficient to provide a solution pH of from about 1.2-5.0 to the sulfated fatty acid surfactant is preferably from about 1-4, as such ratios effectively enable providing sufficient acid to maintain the desired low pH in the diluted solution, and simultaneously sufficient surfactant to aid with cleaning ability of the diluted solution. Additionally, the weight ratio of the one or more natural first organic acids sufficient to provide a solution pH of from about 1.2-5.0 to the one or more fatty acids is preferably from 5-29, and more preferably from 9-28, as such ratios enable formulations that are relatively easy to formulate (formulations with lower ratios may be relatively difficult to formulate as concentrated solutions) and that provide effective hard water tolerance control (formulations with higher ratios may not provide as effective hard water control).

Sanitizing and disinfecting solutions are prepared as highly concentrated solutions, which allow end users to prepare larger quantities of end-use solutions from small amounts of concentrated solution. This also facilitates shipping and handling by minimizing product volume. In a particular embodiment, e.g., the concentrated solution compositions of the invention are designed to be diluting with at least 9 additional parts of water to one part of the concentrate composition to form a diluted solution having a pH of from about 1.5-5.0 used for cleaning, sanitizing, or disinfecting a food or non-food contact surface. In particular embodiments, it is preferred that the highly concentrated solution be prepared as a 30-1000× concentrate (i.e., formulated for dilution of 1 part of concentrated solution in 29 to 999 parts of water, respectively, to prepare the 1× end-use diluted formulation), preferably 40-300×, and most preferably 60-150×.

The food or non-food contact surface may be treated with the 1× end-use diluted sanitizing or disinfecting solution by flooding, dipping, spraying, coating, wiping, or any other means that facilitates contact of the solution with the surface. The surface is exposed to the sanitizing or disinfecting solution for, e.g., from 10 seconds to 15 minutes, preferably 20 seconds to 10 minutes, and most preferably 30 seconds to 5 minutes. After exposure of the surface to the sanitizing or disinfecting solution, the surface may be allowed to dry. If a method such as flooding is used, excess solution is preferably removed (e.g., drained) prior to drying. When food contact surfaces are treated in this manner, they are sanitized or disinfected and the risk of transmission of pathogens is greatly reduced.

The following are examples of several concentrated sanitizing and disinfecting formulations prepared according to this invention:

Example 1: A 64× concentrate is prepared as outlined in the following Table 1.1:

TABLE 1.1

| INGREDIENT | WEIGHT PERCENT | |
|---|---|---|
| | 64X Concentrate | 1X Dilution |
| Citric acid | 25.6 | 0.40 |
| Lauric acid | 1.3 | 0.02 |
| Sodium lauryl sulfate | 10.5 | 0.16 |
| Sodium bicarbonate | 2.6 | 0.04 |
| Isopropanol | 5.5 | 0.09 |
| Water | to 100% | To 100% |

The pH of the resulting concentrated solution is approximately 2.20. The 64× concentrate is then diluted to prepare a 1× end-use diluted sanitizing/disinfecting solution by diluting 1 part of the 64× concentrate with 63 parts of water. The pH of the resulting end-use solution is approximately 2.50.

Example 2: A 64× concentrate is prepared as outlined in the following Table 1.2:

TABLE 1.2

| INGREDIENT | WEIGHT PERCENT | |
|---|---|---|
| | 64X Concentrate | 1X Dilution |
| Citric acid | 25.6 | 0.40 |
| Lauric acid | 1.3 | 0.02 |
| Sodium lauryl sulfate | 10.5 | 0.16 |
| Sodium bicarbonate | 2.6 | 0.04 |
| Isopropanol | 5.5 | 0.09 |
| Sodium sulfate | 5.1 | 0.08 |
| Water | to 100% | To 100% |

The pH of the resulting concentrated solution is approximately 2.21. The 64× concentrate is then diluted to prepare a 1× end-use diluted sanitizing/disinfecting solution by diluting 1 part of the 64× concentrate with 63 parts of water. The pH of the resulting end-use solution is approximately 2.56.

Example 3: A 64× concentrate is prepared as outlined in the following Table 1.3:

TABLE 1.3

| INGREDIENT | WEIGHT PERCENT | |
|---|---|---|
| | 64X Concentrate | 1X Dilution |
| Citric acid | 25.6 | 0.40 |
| Capric acid | 1.3 | 0.02 |
| Sodium lauryl sulfate | 10.5 | 0.16 |
| Sodium bicarbonate | 2.6 | 0.04 |
| Isopropanol | 5.5 | 0.09 |
| Water | to 100% | To 100% |

The pH of the resulting concentrated solution is approximately 2.18. The 64× concentrate is then diluted to prepare a 1× end-use diluted sanitizing/disinfecting solution by diluting 1 part of the 64× concentrate with 63 parts of water. The pH of the resulting end-use solution is approximately 2.53.

Example 4: A 64× concentrate is prepared as outlined in the following Table 1.4:

TABLE 1.4

| INGREDIENT | WEIGHT PERCENT | |
|---|---|---|
| | 64X Concentrate | 1X Dilution |
| Citric acid | 25.6 | 0.40 |
| Capric acid | 1.3 | 0.02 |
| Sodium lauryl sulfate | 10.5 | 0.16 |
| Sodium bicarbonate | 4.8 | 0.08 |
| Isopropanol | 5.5 | 0.09 |
| Sodium bisulfate | 5.2 | 0.04 |
| Water | to 100% | To 100% |

The pH of the resulting concentrated solution is approximately 1.97. The 64× concentrate is then diluted to prepare a 1× end-use diluted sanitizing/disinfecting solution by diluting 1 part of the 64× concentrate with 63 parts of water. The pH of the resulting end-use solution is approximately 2.45.

Example 5: A 128× concentrate is prepared as outlined in the following Table 1.5:

TABLE 1.5

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Sodium bicarbonate | 2.6 | 0.02 |
| Isopropanol | 5.5 | 0.04 |
| Water | to 100% | To 100% |

The pH of the resulting concentrated solution is approximately 2.17. The 128× concentrate is then diluted to prepare a 1× end-use diluted sanitizing/disinfecting solution by diluting 1 part of the 128× concentrate with 127 parts of water. The pH of the resulting end-use solution is approximately 2.66.

Example 6: A 128× concentrate is prepared as outlined in the following Table 1.6:

TABLE 1.6

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Sodium bicarbonate | 2.6 | 0.02 |
| Isopropanol | 5.5 | 0.04 |
| Sodium bisulfate | 5.2 | 0.04 |
| Water | to 100% | To 100% |

The pH of the resulting concentrated solution is 1.96. The 128× concentrate is then diluted to prepare a 1× end-use diluted sanitizing/disinfecting solution by diluting 1 part of the 128× concentrate with 127 parts of water. The pH of the resulting end-use solution is approximately 2.58.

Example 7: A 128× concentrate is prepared as outlined in the following Table 1.7:

TABLE 1.7

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Sodium bicarbonate | 2.9 | 0.02 |
| Isopropanol | 5.5 | 0.04 |
| Water | to 100% | To 100% |

The pH of the resulting concentrated solution is approximately 2.49. The 128× concentrate is then diluted to prepare a 1× end-use diluted sanitizing/disinfecting solution by diluting 1 part of the 128× concentrate with 127 parts of water. The pH of the resulting end-use solution is approximately 2.85.

Example 8: A 128× concentrate is prepared as outlined in the following Table 1.8:

TABLE 1.8

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Sodium bicarbonate | 5.1 | 0.04 |
| Isopropanol | 5.5 | 0.04 |
| Sodium bisulfate | 5.2 | 0.04 |
| Water | to 100% | To 100% |

The pH of the resulting concentrated solution is 2.21. The 128× concentrate is then diluted to prepare a 1× end-use diluted sanitizing/disinfecting solution by diluting 1 part of the 128× concentrate with 127 parts of water. The pH of the resulting end-use solution is approximately 2.61.

Example 9: A concentrate that can be diluted either 1:64 or 1:128 is prepared as outlined in the following Table 1.9:

TABLE 1.9

| INGREDIENT | WEIGHT PERCENT | |
|---|---|---|
| | 128X Concentrate | 1X Dilution |
| Citric acid | 25.6 | 0.20 |
| Lauric acid | 1.3 | 0.01 |

TABLE 1.9-continued

| INGREDIENT | WEIGHT PERCENT | |
|---|---|---|
| | 128X Concentrate | 1X Dilution |
| Sodium lauryl sulfate | 10.5 | 0.08 |
| Sodium citrate | 1.8 | 0.01 |
| Isopropanol | 2.3 | 0.02 |
| Water | to 100% | To 100% |

The pH of the resulting concentrated solution is 2.23. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.32 and 2.41 for the 1:64 and 1:128 dilutions, respectively.

Example 10: A concentrate that can be diluted either 1:64 or 1:128 is prepared as outlined in the following Table 1.10:

TABLE 1.10

| INGREDIENT | WEIGHT PERCENT | |
|---|---|---|
| | 128X Concentrate | 1X Dilution |
| Acetic acid | 21.0 | 0.16 |
| Capric acid | 2.6 | 0.02 |
| Sodium lauryl sulfate | 10.5 | 0.08 |
| Isopropanol | 2.3 | 0.02 |
| Water | to 100% | To 100% |

The pH of the resulting concentrated solution is 2.08. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.58 and 2.63 for the 1:64 and 1:128 dilutions, respectively.

Example 11: A concentrate that can be diluted either 1:64 or 1:128 is prepared as outlined in the following Table 1.11:

TABLE 1.11

| INGREDIENT | WEIGHT PERCENT | |
|---|---|---|
| | 128X Concentrate | 1X Dilution |
| Citric acid | 25.6 | 0.20 |
| Lauric acid | 1.3 | 0.01 |
| Sodium lauryl sulfate | 10.5 | 0.08 |
| Sodium citrate | 1.8 | 0.01 |
| Ethanol | 5.5 | 0.04 |
| Water | to 100% | To 100% |

The pH of the resulting concentrated solution is 2.32. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.36 and 2.51 for the 1:64 and 1:128 dilutions, respectively.

Example 12: A concentrate that can be diluted either 1:64 or 1:128 is prepared as outlined in the following Table 1.12:

TABLE 1.12

| INGREDIENT | WEIGHT PERCENT | |
|---|---|---|
| | 128X Concentrate | 1X Dilution |
| Acetic acid | 21.0 | 0.16 |
| Capric acid | 2.6 | 0.02 |

TABLE 1.12-continued

| INGREDIENT | WEIGHT PERCENT | |
|---|---|---|
| | 128X Concentrate | 1X Dilution |
| Sodium lauryl sulfate | 10.5 | 0.08 |
| Ethanol | 5.5 | 0.04 |
| Water | to 100% | To 100% |

The pH of the resulting concentrated solution is 2.11. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.68 and 2.69 for the 1:64 and 1:128 dilutions, respectively.

Example 13: A concentrate that can be diluted either 1:64 or 1:128 is prepared as outlined in the following Table 1.13:

TABLE 1.13

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Isopropanol | 2.3 | 0.02 |
| Water | to 100% | To 100% |

The pH of the resulting concentrated solution is 1.47. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.23 and 2.30 for the 1:64 and 1:128 dilutions, respectively.

Example 14: A concentrate that can be diluted either 1:64 or 1:128 is prepared as outlined in the following Table 1.14:

TABLE 1.14

| INGREDIENT | WEIGHT PERCENT | |
|---|---|---|
| | 128X Concentrate | 1X Dilution |
| Citric acid | 25.6 | 0.20 |
| Capric acid | 2.6 | 0.02 |
| Sodium lauryl sulfate | 10.5 | 0.08 |
| Ethanol | 2.3 | 0.02 |
| Water | to 100% | To 100% |

The pH of the resulting concentrated solution is 1.45. The concentrate is then diluted 1:64 or 1:128 to prepare the end-use diluted sanitizing/disinfecting solution by diluting 1 part of the concentrate with 63 or 127 parts of water, respectively. The pHs of the resulting end-use solutions are 2.25 and 2.36 for the 1:64 and 1:128 dilutions, respectively.

Scenting of Formulations. Natural essential oils can be added to the sanitizing/disinfecting formulations to provide a natural, pleasing fragrance. Orange oil, lemon oil, and cinnamon oil were added to the formulations at up to 3 percent v/v. All three oils provided a pleasing scent to the concentrated and end-use diluted sanitizing/disinfecting formulations.

Evaluation of Tolerance to Hard Water. The solutions prepared in Examples 1 to 8 were diluted to 1× using an appropriate volume of 375 or 500 ppm artificial hard water. The hard water was prepared shortly before use by combining the appropriate amount of calcium chloride (2.5 or 3.4 mM calcium ion for the 375 or 500 ppm hard water, respectively), magnesium chloride (1.3 or 1.7 mM magnesium ion for the 375 or 500 ppm hard water, respectively), and sodium bicarbonate (3.4 or 4.5 mM for the 375 or 500 ppm hard water, respectively) in distilled water. Each concentrated solution was then diluted in the 375 or 500 ppm hard water. Each solution was tested in triplicate. After dilution, the time to clouding and final appearance of the solutions after 24 hours were measured and the results are presented in Tables 1 and 2. Clouding of the solutions is a result of the interaction of sodium lauryl sulfate with the calcium (primarily) and magnesium ions in the hard water to create an insoluble precipitate that no longer has surfactant properties. In the case of the sanitizing and disinfecting formulations, formation of precipitates is undesired since it greatly reduces the cleaning and antibacterial properties of the solutions. Therefore, clouding is directly related to the ability of the sanitizing and disinfecting solutions to provide the desired efficacy (cleaning and antibacterial properties).

Two control solutions without the fatty acid were used to compare the clouding results of the example formulations. The first control was 10.5% sodium lauryl sulfate in distilled water (Control Solution 1). The second control solution (Control Solution 2) was prepared as outlined in the following Table 2:

TABLE 2

Control Solution 2

| INGREDIENT | WEIGHT % |
|---|---|
| Citric acid | 25.6 |
| Sodium lauryl sulfate | 10.5 |
| Sodium bicarbonate | 4.5 |
| Isopropanol | 5.5 |
| Water | to 100% |

The control solutions were diluted 1 part of concentrated solution in 63 (1:64 dilution) or 127 (1:128 dilution) parts of 375 or 500 ppm hard water. Clouding was defined as not being able to read 2.5 mm tall numbers on the opposite side of a clear polystyrene tube 28.5 mm in diameter containing the 1× diluted solution. Immediately after preparation, all solutions were clear. All example formulations prolonged the time until clouding when compared to the control solutions. Results are presented in the following Tables 3.1 and 3.2.

TABLE 3.1

Time to clouding of sanitizing/disinfecting solutions diluted to 1X end-use concentrations in 375 ppm artificial hard water

| Test Solution | Time to Clouding (minutes) (mean ± SD) | Appearance of Solution at 24 Hours |
|---|---|---|
| 64X Concentrate Diluted to 1X | | |
| Example 1 | 15.7 ± 0.6 | Completely opaque |
| Example 2 | 40.0 ± 3.5 | Completely opaque |
| Example 3 | 39.3 ± 0.6 | Completely opaque |
| Example 4 | 211.7 ± 0.6 | Can discern numbers but not legible |
| Control Solution 1 (64X) | 3.0 ± 0.0 | Completely opaque |
| Control Solution 2 (64X) | 10.0 ± 0.0 | Completely opaque |
| 128X Concentrate Diluted to 1X | | |
| Example 5 | >1,440 | Slightly hazy |
| Example 6 | >1,440 | Slightly hazy |
| Control Solution 1 (128X) | 2.0 ± 0.0 | Completely opaque |
| Control Solution 2 (128X) | 3.7 ± 1.2 | Completely opaque |

TABLE 3.2

Time to clouding of sanitizing/disinfecting solutions diluted to 1X end-use concentrations in 500 ppm artificial hard water

| Test Solution | Time to Clouding (minutes) (mean ± SD) | Appearance of Solution at 24 Hours |
|---|---|---|
| 64X Concentrate Diluted to 1X | | |
| Example 1 | 10.3 ± 0.6 | Completely opaque |
| Example 2 | 21.3 ± 1.5 | Completely opaque |
| Example 3 | 20.7 ± 0.6 | Completely opaque |
| Example 4 | 55.3 ± 0.6 | Can discern numbers but not legible |
| Control Solution 1 (64X) | 2.0 ± 0.0 | Completely opaque |
| Control Solution 2 (64X) | 5.0 ± 1.0 | Completely opaque |
| 128X Concentrate Diluted to 1X | | |
| Example 5 | >1,440 | Slightly hazy |
| Example 6 | >1,440 | Slightly hazy |
| Example 7 | >1,440 | Slightly hazy |
| Example 8 | >1,440 | Slightly hazy |
| Control Solution 1 (128X) | 1.3 ± 0.6 | Completely opaque |
| Control Solution 2 (128X) | 6.0 ± 0.0 | Completely opaque |

Evaluation of Antimicrobial Effectiveness of 1× End-Use Diluted Solutions. The effectiveness of the sanitizing/disinfecting solutions from Examples 1 to 8 diluted to 1× end-use concentrations in 300 or 500 ppm artificial hard water was assessed in a suspension time kill assay against model gram positive (*Staphylococcus aureus*) and gram negative (*Escherichia coli*) bacteria. In brief, the bacterial suspension (~1×10$^{10}$ CFU/ml) was added to 9.9 times the volume of 1× end-use sanitizing/disinfecting solution prepared in 300 or 500 ppm artificial hard water. After 30 seconds, an aliquot of the test solution was removed and neutralized with culture broth. The neutralized solution containing bacteria was then plated on solid agar medium and allowed to incubate at 36±1° C. for 24-48 hours to identify viable colonies. Tables 4.1 and 4.2 summarize the results of duplicate replicates including the log-fold reduction in bacteria for the two replicates combined for each solution and bacterium. All example formulations provided dramatic reductions in bacterial counts with a very short contact time (30 seconds).

TABLE 4.1

Antibacterial efficacy of example sanitizing/disinfecting solutions diluted to 1X in 300 ppm hard water.

| CONCENTRATE SANITIZING/ DISINFECTING SOLUTION | BACTERIUM | REPLICATE | EXPOSURE TIME (SECS) | INITIAL BACTERIAL CONCNTRTN. (CFU/ML) | VIABLE COLONIES (CFU/ML) | AVERAGE $LOG_{10}$ REDUCTION IN BACTERIA |
|---|---|---|---|---|---|---|
| Example 1 (64X) | Staphylococcus aureus | 1 | 30 | $6.65 \times 10^7$ | $2.70 \times 10^4$ | 3.67 |
|  |  | 2 |  |  | $1.58 \times 10^3$ |  |
|  | Eschericia coli | 1 | 30 | $8.80 \times 10^7$ | No growth | >7.25 |
|  |  | 2 |  |  | No growth |  |
| Example 2 (64X) | Staphylococcus aureus | 1 | 30 | $6.65 \times 10^7$ | $1.00 \times 10^1$ | >6.95 |
|  |  | 2 |  |  | No growth |  |
|  | Escherichia coli | 1 | 30 | $8.80 \times 10^7$ | No growth | >7.25 |
|  |  | 2 |  |  | $5.00 \times 10^0$ |  |
| Example 3 (64X) | Staphylococcus aureus | 1 | 30 | $9.90 \times 10^6$ | No growth | >6.30 |
|  |  | 2 |  |  | No growth |  |
| Example 4 (64X) | Staphylococcus aureus | 1 | 30 | $9.90 \times 10^6$ | No growth | >5.90 |
|  |  | 2 |  |  | $2.00 \times 10^1$ |  |
| Example 5 (128X) | Staphylococcus aureus | 1 | 30 | $9.90 \times 10^6$ | No growth | >6.30 |
|  |  | 2 |  |  | No growth |  |
| Example 6 (128X) | Staphylococcus aureus | 1 | 30 | $9.90 \times 10^6$ | No growth | >6.30 |
|  |  | 2 |  |  | No growth |  |
| Example 7 (128X) | Staphylococcus aureus | 1 | 30 | $4.20 \times 10^8$ | No growth | >6.92 |
|  |  | 2 |  |  | No growth |  |
|  | Escherichia coli | 1 | 30 | $1.09 \times 10^9$ | No growth | >7.34 |
|  |  | 2 |  |  | No growth |  |
| Example 8 (128X) | Staphylococcus aureus | 1 | 30 | $4.20 \times 10^8$ | No growth | >6.92 |
|  |  | 2 |  |  | No growth |  |
|  | Escherichia coli | 1 | 30 | $1.09 \times 10^9$ | No growth | >7.34 |
|  |  | 2 |  |  | No growth |  |

TABLE 4.2

Antibacterial efficacy of example sanitizing/disinfecting solutions diluted to 1X in 500 ppm hard water.

| CONCENTRATE SANITIZING/ DISINFECTING SOLUTION | BACTERIUM | REPLICATE | EXPOSURE TIME (SECS) | INITIAL BACTERIAL CONCNTRTN (CFU/ML) | VIABLE COLONIES (CFU/ML) | AVERAGE $LOG_{10}$ REDUCTION IN BACTERIA |
|---|---|---|---|---|---|---|
| Example 7 (128X) | Staphylococcus aureus | 1 | 30 | $4.20 \times 10^8$ | No growth | >6.92 |
|  |  | 2 |  |  | No growth |  |
|  | Escherichia coli | 1 | 30 | $1.09 \times 10^9$ | No growth | >7.34 |
|  |  | 2 |  |  | No growth |  |
| Example 8 (128X) | Staphylococcus aureus | 1 | 30 | $4.20 \times 10^8$ | No growth | >6.92 |
|  |  | 2 |  |  | No growth |  |
|  | Escherichia coli | 1 | 30 | $1.09 \times 10^9$ | No growth | >7.34 |
|  |  | 2 |  |  | No growth |  |

Evaluation of Corrosion of Concentrated and 1× End-Use Diluted Solutions. The corrosiveness of several of the concentrated and 1× end-use diluted solutions was tested by immersing pieces of stainless steel and aluminum in the concentrated or 1× end-use diluted solutions. The visual appearance of the metal pieces was assessed over time as summarized in Tables 5.1 and 5.2.

TABLE 5.1

Appearance of stainless steel after constant immersion in concentrated or 1X end-use diluted solutions.

| Test Solution | Appearance | | | | | |
|---|---|---|---|---|---|---|
|  | 1 Day | 2 Days | 4 Days | 7 Days | 14 Days | 21 Days |
| Example 1 | | | | | | |
| 64X concentrate | Normal | Normal | Normal | Normal | Normal | Normal |
| 1X end-use dilution | Normal | Normal | Normal | Normal | Normal | Normal |

TABLE 5.1-continued

Appearance of stainless steel after constant immersion in concentrated or 1X end-use diluted solutions.

| Test Solution | Appearance | | | | | |
|---|---|---|---|---|---|---|
| | 1 Day | 2 Days | 4 Days | 7 Days | 14 Days | 21 Days |
| Example 5 | | | | | | |
| 128X concentrate | Normal | Normal | Normal | Normal | Normal | Normal |
| 1X end-use dilution | Normal | Normal | Normal | Normal | Normal | Normal |
| Example 6 | | | | | | |
| 128X concentrate | Normal | Normal | Normal | Normal | Normal | Normal |
| 1X end-use dilution | Normal | Normal | Normal | Normal | Normal | Normal |
| Positive Controls | | | | | | |
| 10.5% hypochlorite | Minimal yellow surface coating. | Minimal yellow surface coating. | Moderate yellow surface coating. Moderate black corrosion. | Marked yellow surface coating. Moderate black corrosion. | Marked yellow surface coating. Moderate black corrosion. | Marked yellow surface coating. Moderate black corrosion. |
| 0.246% hypochlorite | Slight yellow surface coating. | Slight yellow surface coating. | Minimal yellow surface coating. Slight black corrosion. | Moderate yellow surface coating. Slight black corrosion. | Marked yellow surface coating. Minimal black corrosion. | Marked yellow surface coating. Minimal black corrosion. |
| 0.042% hypochlorite | Normal | Normal | Slight yellow surface coating. | Slight yellow surface coating. | Slight yellow surface coating. | Slight yellow surface coating. |
| Negative Control | | | | | | |
| Distilled Water | Normal | Normal | Normal | Normal | Normal | Normal |

Note:
for severity of findings, slight < minimal < moderate < marked

TABLE 5.2

Appearance of aluminum after constant immersion in concentrated or 1X end-use diluted solutions.

| Test Solution | Appearance | | | | | |
|---|---|---|---|---|---|---|
| | 1 Day | 2 Days | 4 Days | 7 Days | 14 Days | 21 Days |
| Example 1 | | | | | | |
| 64X concentrate | Normal | Normal | Normal | Normal | Slight white film. | Slight white film. |
| 1X end-use dilution | Normal | Normal | Normal | Normal | Slight gray film. | Slight gray film. |
| Example 5 | | | | | | |
| 128X concentrate | Normal | Normal | Normal | Normal | Slight white film. | Slight white film. |
| 1X end-use dilution | Normal | Normal | Normal | Normal | Normal | Slight gray film. |
| Example 6 | | | | | | |
| 128X concentrate | Normal | Normal | Normal | Normal | Slight white film. | Slight white film. |
| 1X end-use dilution | Normal | Normal | Normal | Normal | Slight gray film. | Slight gray film. |

TABLE 5.2-continued

Appearance of aluminum after constant immersion in concentrated or 1X end-use diluted solutions.

| Test Solution | Appearance | | | | | |
|---|---|---|---|---|---|---|
| | 1 Day | 2 Days | 4 Days | 7 Days | 14 Days | 21 Days |
| Positive Controls | | | | | | |
| 10.5% hypochlorite | Moderate black and yellow surface coating and spots. | Marked black and yellow corrosion. | Marked black and yellow corrosion. | Marked black and white corrosion. | Marked black and white corrosion. | Marked black and white corrosion. |
| 0.246% hypochlorite | Moderate black surface coating. | Moderate black surface coating. | Marked black surface coating. | Marked black surface coating. | Marked black surface coating. | Marked black surface coating. |
| 0.042% hypochlorite | Slight gray surface coating. | Minimal black surface coating. | Marked black surface coating. | Marked black surface coating. | Marked black surface coating. | Marked black surface coating. |
| Negative Control | | | | | | |
| Distilled Water | Normal | Normal | Normal | Normal | Normal | Slight white film. |

Note:
for severity of findings, slight < minimal < moderate < marked

Stability of Concentrated Solutions During Elevated Temperature Storage. The stability of the concentrated solutions was tested by placing example solutions at 54° C. for 2 weeks and assessing when the solutions became cloudy or separated, both of which indicate instability of the solutions. The temperature and duration of the test was selected since the US Environmental Protection Agency recommends these parameters when assessing the stability of sanitizer/disinfectant formulations. Tables 6 and 7 demonstrate that isopropanol or ethanol increase the elevated temperature stability of the acid-anionic surfactant-fatty acid formulations. In addition, Table 8 demonstrates that the concentration of alcohol is critical since too low and stability is decreased.

TABLE 6

Influence of isopropanol on the elevated temperature stability (54° C.) of acid-anionic surfactant-fatty acid formulations

| Aqueous Formulation | Time to Cloud or Separate (Days) |
|---|---|
| 25.6% citric acid<br>10.5% sodium lauryl sulfate | 10 |
| 25.6% citric acid<br>10.5% sodium lauryl sulfate<br>7% (v/v) isopropanol | Stable and clear at 2 weeks |
| 25.6% citric acid<br>10.5% sodium lauryl sulfate<br>2.8% (v/v) decanoic acid | 1 |
| 25.6% citric acid<br>10.5% sodium lauryl sulfate<br>7% (v/v) isopropanol<br>2.8% (v/v) decanoic acid | Stable and clear at 2 weeks |
| 25.6% citric acid<br>10.5% sodium lauryl sulfate<br>1.4% (v/v) decanoic acid | 6 |
| 25.6% citric acid<br>10.5% sodium lauryl sulfate<br>7% (v/v) isopropanol<br>1.4% (v/v) decanoic acid | Stable and clear at 2 weeks |

TABLE 7

Influence of isopropanol or ethanol on the elevated temperature stability (54° C.) of acid-anionic surfactant-fatty acid formulations

| Aqueous Formulation | Time to Cloud or Separate (Days) |
|---|---|
| 25.6% citric acid<br>10.5% sodium lauryl sulfate | 11 |
| 25.6% citric acid<br>10.5% sodium lauryl sulfate<br>7% (v/v) ethanol | Stable and clear at 2 weeks |
| 25.6% citric acid<br>10.5% sodium lauryl sulfate<br>2.8% (v/v) decanoic acid | 2 |
| 25.6% citric acid<br>10.5% sodium lauryl sulfate<br>7% (v/v) ethanol<br>2.8% (v/v) decanoic acid | Stable and clear at 2 weeks |
| 25.6% citric acid<br>10.5% sodium lauryl sulfate<br>1.3% (w/v) lauric acid | 8 |
| 25.6% citric acid<br>10.5% sodium lauryl sulfate<br>7% (v/v) isopropanol<br>1.3% (w/v) lauric acid | Stable and clear at 2 weeks |

TABLE 8

Influence of varying isopropanol concentrations on the elevated temperature stability (54° C.) of acid-anionic surfactant-fatty acid formulations

| Aqueous Formulation | Time to Cloud or Separate (Days) |
|---|---|
| 25.6% citric acid<br>10.5% sodium lauryl sulfate<br>2.8% (v/v) decanoic acid | 2 |
| 25.6% citric acid<br>10.5% sodium lauryl sulfate<br>0.1% (v/v) isopropanol<br>2.8% (v/v) decanoic acid | 1 |
| 25.6% citric acid<br>10.5% sodium lauryl sulfate | 1 |

TABLE 8-continued

Influence of varying isopropanol concentrations on the elevated temperature stability (54° C.) of acid-anionic surfactant-fatty acid formulations

| Aqueous Formulation | Time to Cloud or Separate (Days) |
|---|---|
| 0.2% (v/v) isopropanol 2.8% (v/v) decanoic acid 25.6% citric acid 10.5% sodium lauryl sulfate | 4 |
| 1% (v/v) isopropanol 2.8% (v/v) decanoic acid 25.6% citric acid 10.5% sodium lauryl sulfate | Stable and clear at 2 weeks |
| 2% (v/v) isopropanol 2.8% (v/v) decanoic acid 25.6% citric acid 10.5% sodium lauryl sulfate | Stable and clear at 2 weeks |
| 3% (v/v) isopropanol 2.8% (v/v) decanoic acid 25.6% citric acid 10.5% sodium lauryl sulfate | Stable and clear at 2 weeks |
| 4% (v/v) isopropanol 2.8% (v/v) decanoic acid 25.6% citric acid 10.5% sodium lauryl sulfate | Stable and clear at 2 weeks |
| 5% (v/v) isopropanol 2.8% (v/v) decanoic acid 25.6% citric acid 10.5% sodium lauryl sulfate | Stable and clear at 2 weeks |
| 6% (v/v) isopropanol 2.8% (v/v) decanoic acid 25.6% citric acid 10.5% sodium lauryl sulfate | Stable and clear at 2 weeks |
| 7% (v/v) isopropanol 2.8% (v/v) decanoic acid | |

Evaluation of Foaming of 1× End-Use Diluted Solutions. The foaming of 1× end-use diluted solutions of Examples 1 to 8 was assessed by applying 15 ml of each 1× end-use diluted solution to a stainless steel countertop. A rectangular paper towel with the dimensions of 10.5 by 11 inches was used to wipe the solution in a circular motion in a clockwise followed by a counterclockwise direction on the countertop. Foaming was visually assessed along with the time to dissipation of foaming and residue remaining on the countertop. As positive controls, a solution of 10.5% sodium lauryl sulfate diluted in water to 0.164% (64× control) or 0.082% (128× control) were used. Results are presented in Table 9.

TABLE 9

| Test Solution | Test Concentration | Foaming | Time to Foam Dissipation (seconds) | Residue After Drying |
|---|---|---|---|---|
| 64X Concentrate Diluted to 1X | | | | |
| Example 1 (64X concentrate) | 1X | Minimal | 30 | None |
| Example 2 (64X concentrate) | 1X | Minimal | 22 | None |
| Example 3 (64X concentrate) | 1X | Minimal | 16 | None |
| Example 4 (64X concentrate) | 1X | Minimal | 44 | None |
| Positive Control (64X) | 0.164% SLS | Moderate | 106 | None |
| 128X Concentrate Diluted to 1X | | | | |
| Example 5 (128X concentrate) | 1X | Slight | 5 | None |
| Example 6 (128X concentrate) | 1X | Slight | 5 | None |
| Example 7 (128X concentrate) | 1X | Slight | 6 | None |
| Example 8 (128X concentrate) | 1X | Slight | 5 | None |
| Positive Control (128X) | 0.082% SLS | Minimal | 52 | None |

Note:
foaming was assessed as slight < minimal < moderate < marked; SLS = sodium lauryl sulfate While the invention has been described in connection with several presently preferred embodiments thereof, those skilled in the art will appreciate that many modifications and changes may be made without departing from the true spirit and scope of the invention which accordingly is intended to be defined solely by the appended claims.

The invention claimed is:

1. A sanitizing and disinfecting solution concentrate composition, comprising:
   at least 10 wt % water;
   21-30 wt % of one or more of citric acid, fumaric acid, humic acid, acetic acid, and ascorbic acid;
   about 5-30 wt % lauryl sulfate;
   about 1-5 w t% of one or more of caprylic acid, capric acid, and lauric acid;
   about 2-10 wt % of one or more of ethanol and isopropanol; and
   a basic buffering agent;
   wherein:
   a 1:64 to 1:128 dilution of the concentrate composition in water reduces *Staphylococcus aureus* growth by at least 3.67 orders of magnitude upon contacting the *Staphylococcus aureus* with the dilution of the concentrate composition for 30 seconds; and
   a 1:64 to 1:128 dilution of the concentrate composition in water reduces *Escherichia coli* growth by at least 7.25 orders of magnitude upon contacting the *Escherichia coli* with the dilution of the concentrate composition for 30 seconds.

2. The sanitizing and disinfecting solution concentrate composition of claim 1, wherein the composition consists of:
   water;
   one or more of citric acid, fumaric acid, humic acid, acetic acid, and ascorbic acid;
   lauryl sulfate;
   one or more of caprylic acid, capric acid, and lauric acid;
   one or more of ethanol and isopropanol;
   the basic buffering agent;
   optionally, a buffering salt which is a source of sodium, potassium, magnesium, or calcium ions;
   optionally, sulfate or bisulfate; and
   optionally, an essential oil.

3. A sanitizing and disinfecting solution concentrate composition, comprising:
   at least 10 wt % water;
   citric acid at a concentration of 21 to 30 wt %;
   lauryl sulfate at a concentration of about 5 to 30 wt %;
   capric acid at a concentration of about 1 to 5 wt %;
   isopropanol at a concentration of about 2 to 10 wt %; and
   carbonate, bicarbonate, or both carbonate and bicarbonate;

wherein:
  a 1:64 to 1:128 dilution of the concentrate composition in water reduces *Staphylococcus aureus* growth by at least 6.30 orders of magnitude upon contacting the *Staphylococcus aureus* with the dilution of the concentrate composition for 30 seconds; and
  a 1:64 to 1:128 dilution of the concentrate composition in water reduces *Escherichia coli* growth by at least 7.34 orders of magnitude upon contacting the *Escherichia coli* with the dilution of the concentrate composition for 30 seconds.

4. A liquid sanitizer and cleaning solution concentrate composition, comprising:
  citric acid at a concentration of 21% to 30% by weight;
  capric acid at a concentration of about 0.1% to about 5% by weight;
  lauryl sulfate at a concentration of about 5% to about 30% by weight;
  isopropanol at a concentration of about 1% to about 20% by weight;
  a basic buffering agent; and
  water at a concentration of at least about 10% by weight,
  wherein:
  the pH of the composition is about 1.2 to about 5.0;
  a 1:64 to 1:128 dilution of the concentrate composition in water reduces *Staphylococcus aureus* growth by at least 6.30 orders of magnitude upon contacting the *Staphylococcus aureus* with the dilution of the concentrate composition for 30 seconds; and
  a 1:64 to 1:128 dilution of the concentrate composition in water reduces *Escherichia coli* growth by at least 7.34 orders of magnitude upon contacting the *Escherichia coli* with the dilution of the concentrate composition for 30 seconds.

5. The liquid sanitizer and cleaning solution concentrate composition of claim 4, wherein the composition is essentially free of chlorine, chlorine dioxide, chlorinated compounds, halogenated compounds, and peracetic acid.

6. The liquid sanitizer and cleaning solution concentrate composition of claim 4, wherein the composition is essentially free of corrosives.

7. The liquid sanitizer and cleaning solution concentrate composition of claim 4, wherein each molecule of the composition either (1) exists in nature or (2) can be produced by the saponification and/or sulfation of a fatty acid that exists in nature.

8. The liquid sanitizer and cleaning solution concentrate composition of claim 4, consisting essentially of:
  citric acid;
  capric acid;
  lauryl sulfate;
  isopropanol;
  water;
  carbonate, bicarbonate, or both carbonate and bicarbonate;
  optionally, bisulfate;
  optionally, an essential oil;
  optionally, a pH buffer;
  inorganic counterions of any of the foregoing; and
  protonated and/or deprotonated forms of any of the foregoing.

9. The liquid sanitizer and cleaning solution concentrate composition of claim 4, consisting of:
  citric acid;
  capric acid;
  lauryl sulfate;
  isopropanol;
  water;
  carbonate, bicarbonate, or both carbonate and bicarbonate;
  optionally, bisulfate;
  optionally, an essential oil;
  optionally, a pH buffer;
  inorganic counterions of any of the foregoing; and
  protonated and/or deprotonated forms of any of the foregoing.

10. The liquid sanitizer and cleaning solution concentrate composition of claim 4, consisting of:
  citric acid;
  capric acid;
  lauryl sulfate;
  isopropanol;
  water;
  bicarbonate;
  inorganic counterions of any of the foregoing; and
  protonated and/or deprotonated forms of any of the foregoing.

11. The sanitizing and disinfecting solution concentrate composition of claim 1, wherein the composition is essentially free of chlorine, chlorine dioxide, chlorinated compounds, halogenated compounds, and peracetic acid.

12. The sanitizing and disinfecting solution concentrate composition of claim 1, wherein the composition is essentially free of corrosives.

13. The sanitizing and disinfecting solution concentrate composition of claim 1, wherein each molecule of the composition either (1) exists in nature or (2) can be produced by the saponification and/or sulfation of a fatty acid that exists in nature.

14. The sanitizing and disinfecting solution concentrate composition of claim 1, consisting essentially of:
  one or more of citric acid, fumaric acid, humic acid, acetic acid, and ascorbic acid;
  lauryl sulfate;
  one or more of caprylic acid, capric acid, and lauric acid;
  one or more of ethanol and isopropanol;
  water;
  carbonate, bicarbonate, or both carbonate and bicarbonate;
  optionally, bisulfate;
  optionally, an essential oil;
  optionally, a pH buffer;
  inorganic counterions of any of the foregoing; and
  protonated and/or deprotonated forms of any of the foregoing.

15. The sanitizing and disinfecting solution concentrate composition of claim 3, wherein the composition is essentially free of chlorine, chlorine dioxide, chlorinated compounds, halogenated compounds, and peracetic acid.

16. The sanitizing and disinfecting solution concentrate composition of claim 3, wherein the composition is essentially free of corrosives.

17. The sanitizing and disinfecting solution concentrate composition of claim 3, wherein each molecule of the composition either (1) exists in nature or (2) can be produced by the saponification and/or sulfation of a fatty acid that exists in nature.

18. The sanitizing and disinfecting solution concentrate composition of claim 3, consisting essentially of:
  citric acid;
  capric acid;
  lauryl sulfate;
  isopropanol;

carbonate, bicarbonate, or both carbonate and bicarbonate;
water;
optionally, bisulfate;
optionally, an essential oil;
optionally, a pH buffer;
inorganic counterions of any of the foregoing; and
protonated and/or deprotonated forms of any of the foregoing.

19. The sanitizing and disinfecting solution concentrate composition of claim 3, consisting of:
citric acid;
capric acid;
lauryl sulfate;
isopropanol;
water;
sodium citrate;
carbonate, bicarbonate, or both carbonate and bicarbonate;
optionally, bisulfate;
optionally, an essential oil;
optionally, a pH buffer;
inorganic counterions of any of the foregoing; and
protonated and/or deprotonated forms of any of the foregoing.

20. The sanitizing and disinfecting solution concentrate composition of claim 3, consisting of:
citric acid;
capric acid;
lauryl sulfate;
isopropanol;
water;
carbonate, bicarbonate, or both carbonate and bicarbonate;
inorganic counterions of any of the foregoing; and
protonated and/or deprotonated forms of any of the foregoing.

* * * * *